US008591874B2

(12) United States Patent
Oblong et al.

(10) Patent No.: US 8,591,874 B2
(45) Date of Patent: Nov. 26, 2013

(54) INHIBITION OF MAMMALIAN HAIR GROWTH

(75) Inventors: John Erich Oblong, Loveland, OH (US); Sara Johnson McPhail, West Chester, OH (US); Shannon Christine McArthur, Indian Springs, OH (US); Charles Carson Bascom, Hamilton, OH (US); David Joseph Eickhoff, Ft. Mitchell, KY (US); John McMillan McIver, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/344,771

(22) Filed: Feb. 1, 2006

(65) Prior Publication Data
US 2006/0127431 A1   Jun. 15, 2006

Related U.S. Application Data

(63) Continuation of application No. 10/783,151, filed on Feb. 19, 2004, now abandoned.

(60) Provisional application No. 60/451,910, filed on Mar. 4, 2003.

(51) Int. Cl.
*A61K 8/73* (2006.01)
*A61K 8/00* (2006.01)
*A61Q 5/00* (2006.01)
*A61Q 9/00* (2006.01)

(52) U.S. Cl.
USPC ........................................ 424/70.17; 424/70.1

(58) Field of Classification Search
None
See application file for complete search history.

(56) References Cited

U.S. PATENT DOCUMENTS

| | | | |
|---|---|---|---|
| 2,798,053 A | | 7/1957 | Brown |
| 2,831,854 A | | 4/1958 | Tucker et al. |
| 3,155,591 A | | 11/1964 | Hilfer |
| 3,755,560 A | | 8/1973 | Dickert et al. |
| 3,929,678 A | | 12/1975 | Laughlin et al. |
| 3,959,461 A | | 5/1976 | Bailey et al. |
| 3,963,699 A | | 6/1976 | Rizzi et al. |
| 4,005,195 A | | 1/1977 | Jandacek |
| 4,005,196 A | | 1/1977 | Jandacek et al. |
| 4,206,215 A | | 6/1980 | Bailey |
| 4,387,090 A | | 6/1983 | Bolich, Jr. |
| 4,421,769 A | | 12/1983 | Dixon et al. |
| 4,505,924 A | | 3/1985 | Taylor |
| 4,507,321 A | * | 3/1985 | Raisfeld .................. 514/673 |
| 4,509,949 A | | 4/1985 | Huang et al. |
| 4,517,360 A | | 5/1985 | Volpenhein |
| 4,518,772 A | | 5/1985 | Volpenhein |
| 4,557,853 A | | 12/1985 | Collins |
| 4,599,379 A | | 7/1986 | Flesher et al. |
| 4,628,078 A | | 12/1986 | Glover et al. |
| 4,708,966 A | | 11/1987 | Loomans et al. |
| 4,797,300 A | | 1/1989 | Jandacek et al. |
| 4,835,148 A | | 5/1989 | Barford et al. |
| 4,835,206 A | | 5/1989 | Farrar et al. |
| 4,847,071 A | | 7/1989 | Bissett et al. |
| 4,849,484 A | | 7/1989 | Heard |
| 4,937,370 A | | 6/1990 | Sabatelli |
| 4,960,764 A | | 10/1990 | Figueroa, Jr. et al. |
| 4,976,953 A | | 12/1990 | Orr et al. |
| 4,999,186 A | | 3/1991 | Sabatelli et al. |
| 5,004,734 A | | 4/1991 | Philippe |
| 5,011,681 A | | 4/1991 | Ciotti et al. |
| 5,073,371 A | | 12/1991 | Turner et al. |
| 5,073,372 A | | 12/1991 | Turner et al. |
| 5,087,445 A | | 2/1992 | Haffey et al. |
| 5,100,660 A | | 3/1992 | Hawe et al. |
| 5,120,532 A | | 6/1992 | Wells et al. |
| 5,151,209 A | | 9/1992 | McCall et al. |
| 5,151,210 A | | 9/1992 | Steuri et al. |
| 5,189,066 A | | 2/1993 | Kelm et al. |
| 5,204,093 A | | 4/1993 | Victor |
| 5,280,045 A | | 1/1994 | Dobson et al. |
| 5,306,515 A | | 4/1994 | Letton et al. |
| 5,306,516 A | | 4/1994 | Letton et al. |

(Continued)

FOREIGN PATENT DOCUMENTS

EP   0228868 A2   7/1987
EP   0330369 A1   8/1989

(Continued)

OTHER PUBLICATIONS

Agmatine structure, from Sigma.*
Paus et al. "The Biology of Hair Follicles"; Mechanism of Diseases, vol. 341, No. 7, pp. 491-497, Aug. 12, 1999.*
Agmatine structure, from Sigma. Downloaded on Oct. 28, 2008, previously provided.*
US 5,674,447, 10/1997, Ahluwalia (withdrawn).
US 5,305,514, 04/1994, Letton et al. (withdrawn).

(Continued)

*Primary Examiner* — Isis Ghali
(74) *Attorney, Agent, or Firm* — John G. Powell; Angela K. Haughey; Melody A. Jones

(57) ABSTRACT

The present invention relates to a topical skin care composition containing a safe and effective amount of a skin care active comprising agmatine, and its salt; a safe and effective amount of a first additional skin care active selected from the group consisting of BHT or BHA, hexamidine, cetyl pyridinium chloride, green tea catechins, phytosterols, ursolic acid, compounds derived from plant extracts, their salts and derivatives; and a dermatologically acceptable carrier for the agmatine composition. The present invention also relates to methods of using such agmatine compositions to regulate hair growth and the condition of mammalian skin. The methods generally comprise the step of topically applying the composition to the skin of a mammal needing such treatment, a safe and effective amount of such compositions.

5 Claims, No Drawings

(56) References Cited

U.S. PATENT DOCUMENTS

| | | | |
|---|---|---|---|
| 5,476,876 A | 12/1995 | Pikul et al. | |
| 5,487,884 A | 1/1996 | Bissett et al. | |
| 5,510,361 A | 4/1996 | Scherz et al. | |
| 5,554,608 A | 9/1996 | Ahluwalia | |
| 5,607,980 A | 3/1997 | McAtee et al. | |
| 5,652,228 A | 7/1997 | Bissett | |
| 5,674,477 A | 10/1997 | Ahluwalia | |
| 5,681,852 A | 10/1997 | Bissett | |
| 5,684,204 A | 11/1997 | Matthews et al. | |
| 5,686,082 A | 11/1997 | N'Guyen | |
| 5,686,367 A | 11/1997 | Hayashi | |
| 5,709,847 A | 1/1998 | Bissett | |
| 5,776,442 A | 7/1998 | Ahluwalia | |
| 5,821,250 A | 10/1998 | Wu et al. | |
| 5,897,857 A | 4/1999 | Hillebrand et al. | |
| 5,939,082 A | 8/1999 | Oblong et al. | |
| 5,958,946 A * | 9/1999 | Styczynski et al. | 514/311 |
| 5,972,957 A | 10/1999 | Wu et al. | |
| 5,981,547 A | 11/1999 | Wu et al. | |
| 6,060,471 A | 5/2000 | Styczynski | |
| 6,060,547 A | 5/2000 | Canter et al. | |
| 6,068,834 A | 5/2000 | Kvalnes et al. | |
| 6,075,052 A | 6/2000 | Suzuki et al. | |
| 6,149,896 A * | 11/2000 | Riklis et al. | 424/59 |
| 6,207,596 B1 | 3/2001 | Rourke | |
| 6,375,948 B1 | 4/2002 | Tsuji | |
| 6,495,149 B1 | 12/2002 | Scavone et al. | |
| 6,716,414 B2 * | 4/2004 | Lewis et al. | 424/45 |
| 6,716,441 B1 | 4/2004 | Osborne | |
| 2003/0118539 A1* | 6/2003 | Fahl et al. | 424/70.17 |
| 2003/0165447 A1 | 9/2003 | Scavone et al. | |
| 2003/0190337 A1 | 10/2003 | Bissett | |
| 2005/0003024 A1 | 1/2005 | Oblong et al. | |
| 2006/0127431 A1 | 6/2006 | Oblong | |
| 2008/0188505 A1 | 8/2008 | Oblong | |

FOREIGN PATENT DOCUMENTS

| | | |
|---|---|---|
| JP | 63203608 | 8/1988 |
| JP | 11-035425 | 2/1999 |
| JP | 11-322548 | 11/1999 |
| JP | 2000-302659 | 10/2000 |
| JP | 2000-319154 | 11/2000 |
| JP | 2002-249414 | 9/2002 |
| WO | WO-91/16034 A1 | 10/1991 |
| WO | WO-91/16035 A1 | 10/1991 |
| WO | WO-95/13048 A1 | 5/1995 |
| WO | WO-95/23780 A2 | 9/1995 |
| WO | WO-95/34280 A1 | 12/1995 |
| WO | WO-96/01101 A1 | 1/1996 |
| WO | WO 96/26705 A1 | 9/1996 |
| WO | WO 97/19672 A1 | 6/1997 |
| WO | WO-97/39733 A1 | 10/1997 |
| WO | WO-99/37277 | 7/1999 |
| WO | WO 01/43717 A1 | 6/2001 |
| WO | 03092668 | 5/2002 |
| WO | 03013245 | 2/2003 |
| WO | WO 03/013245 A1 | 2/2003 |
| WO | WO 03/092668 A1 | 11/2003 |

OTHER PUBLICATIONS

Sagarin, et al., Cosmetics, Science and Technology, 2nd Edition, vol. 1, pp. 32-43 (1972).

McCutcheon's Detergents and Emulsifiers, North American Edition, pp. 317-324 (1986).

Federal Register, vol. 43, No. 166, pp. 38206-38269, Aug. 25, 1978.

Dahms et al., "New Formulation Possibilities Offered by Silicone Copolyols," Cosmetics & Toiletries, vol. 110, pp. 91-100, Mar. 1995.

Carlotti et al., "Optimization of W/O-S Emulsions and Study of the Quantitative Relationships between Ester Structure and Emulsion Properties," J. Dispersion Science and Technology, 13(3), pp. 315-336 (1992).

Hameyer, P. "Comparative Technological Investigations of Organic and Organosilicone Emulsifiers in Cosmetic Water-in-Oil Emulsion Preparations," HAPPI 28 (4), pp. 88, 90, 92, and 94 (Apr. 1991).

Smid-Korbar et al., "Efficiency and Usability of Silicone Surfactants in Emulsions," Provisional Communication, International Journal of Cosmetic Science, vol. 12, No. 3, 135-139 (Jun. 1990).

Krzysik et al., "A New Silicone Emulsifier for Water-in-Oil Systems," Drug and Cosmetic Industry, vol. 146 (4), pp. 28-35, 79 and 81 (Apr. 1990).

CTFA International Cosmetic Ingredient Dictionary, Fourth Edition, pp. 12 and 80 (1991).

Sagarin, Cosmetics, Science and Technology, 2nd Edition, vol. 1, pp. 72-73 (1972).

The Merck Index, Tenth Edition, entry 3167, p. 463 (1983).

U.S. Appl. No. 08/570,275, filed Dec. 11, 1995, Zukowski et al.

* cited by examiner

INHIBITION OF MAMMALIAN HAIR GROWTH

CROSS REFERENCE TO RELATED APPLICATION(S)

This application is a continuation of U.S. application Ser. No. 10/783,151, filed on Feb. 19, 2004 now abandoned; which claims the benefit of U.S. Provisional Application Ser. No. 60/451,910, filed Mar. 4, 2003.

TECHNICAL FIELD

The present invention relates to topical compositions containing a combination of skin care actives, particularly agmatine and its salts, in combination with other skin care actives such as butylated hydroxytoluene (BHT) and butylated hydroxyanisole (BHA), cetyl pyridinium chloride, hexamidine, phytosterols, compounds derived from plant extracts, green tea catechin compounds, ursolic acid, and free fatty acids. Such compositions are useful for regulating the condition of keratinous tissue, including, but not limited to, regulating mammalian hair growth, preferably inhibiting and/or retarding hair growth and/or reducing shaving frequency.

BACKGROUND OF INVENTION

As is well-known in the art, normal hair growth occurs by a cycle of activity which involves alternating periods of growth and rest. This cycle is often divided into three main stages which are known as anagen, catagen, and telogen. Anagen is the growth phase of the cycle and may be characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth is ceased. The next phase, telogen, is often characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. This cycle is repeated throughout hair growth. Wherein hair growth ceases, most of the hair follicles reside in telogen and anagen is not engaged, thus causing the onset of full or partial baldness.

A main function of mammalian hair growth is to provide environmental protection. However, that function has been lost in humans, in whom, hair is kept or removed from various parts of the body, essentially for cosmetic reasons. For example, for women in the United States, it is generally preferred to have hair on the scalp, but not on the legs, underarms, or certain areas of the face.

Various procedures and personal care products have been developed to remove unwanted hair, including shaving, electrolysis, depilatory creams or lotions, depilatory devices, waxing, plucking, therapeutic androgens, and laser hair removal. However, such conventional procedures frequently have drawbacks associated with them. Shaving, for instance, may cause nicks, cuts, rash and irritation and often leaves an undesirable stubble. Electrolysis and laser hair removal can keep a treated area free of hair for prolonged periods of time, but can be either expensive, painful, and/or sometimes leave scarring. Waxing and plucking are painful and are poor options for shorter hair. Anti-androgens, used to treat female hirsutism, can have unpleasant physical side effects as well as possible birth defect implications. Since in non-hirsutistic females, the role of androgens is not required for normal hair growth, there is a need for technologies that do not function via androgen mediated pathways due to the birth defect implications. Depilatory devices can be painful to use and are not well-suited for many areas of the body including underarms and face. Finally, depilatory creams, although effective, are messy to apply and typically are not recommended for frequent use due to their high irritancy potential.

Therefore, a need exists for a safe, effective way to not only regulate the condition of mammalian keratinous tissue, but also to retard, inhibit, and/or stop unwanted mammalian hair growth on designated areas of the body.

Surprisingly, it has now been discovered that compositions containing agmatine and its sulfate salt, in combination with other selected skin care actives, are useful for regulating mammalian hair growth, including retarding, inhibiting, or eliminating hair growth. Without being limited by theory, it is believed that agmatine is able to modulate hair growth by inhibiting protease activity in and surrounding the hair follicular unit in mammalian skin. Proteases are key components in restructuring of the extracellular matrix during follicular progression through the dermis of skin in early anagen. Additionally, proteases play a role in angiogenesis, a key process for vascularization of the hair follicle during early anagen as well as maintenance of the vasculature bed during all of anagen. Additionally, it is believed that agmatine can modulate hair growth by upregulating antizyme, a protein that regulates and degrades ornithine decarboxylase (ODC). Ornithine decarboxylase is a critical enzyme for cell viability. Agmatine can therefore inhibit ODC activity indirectly by upregulating antizyme. Thus, agmatine plays a role in blocking structural remodeling of the hair follicular unit as well as inhibiting the vascularization of the follicular unit and hair follicle cellular proliferation via ODC, thereby altering mammalian hair growth properties.

Surprisingly, it has also been discovered that select skin care compositions such as BHT or BHA, cetyl pyridinium chloride, hexamidine, and ursolic acid can be used alone for regulating mammalian hair growth, including retarding, inhibiting, or eliminating hair growth.

None of the existing art provides all the advantages and benefits of the present invention.

SUMMARY

The present invention relates to a topical skin care composition containing a safe and effective amount of a skin care active comprising agmatine, and its salt; a safe and effective amount of a first additional skin care active selected from the group consisting of BHT or BHA, hexamidine, cetyl pyridinium chloride, green tea catechins, phytosterols, ursolic acid, compounds derived from plant extracts, their salts and derivatives; and a dermatologically acceptable carrier for the agmatine composition.

The present invention also relates to methods of using such agmatine compositions to regulate hair growth and the condition of mammalian skin. Said methods generally comprise the step of topically applying the composition to the skin of a mammal needing such treatment, a safe and effective amount of such compositions.

The present invention relates to a topical skin care composition containing a safe and effective amount of a skin care active comprising cetyl pyridinium chloride, and its salt; a safe and effective amount of a first additional skin care active selected from the group consisting of ursolic acid and compounds derived from plant extracts, their salts and derivatives; and a dermatologically acceptable carrier for the cetyl pyridinium chloride composition.

The present invention also relates to methods of using such cetyl pyridinium chloride compositions to regulate hair growth and the condition of mammalian skin. Said methods generally comprise the step of topically applying the composition to the skin of a mammal needing such treatment, a safe and effective amount of such compositions.

The present invention also relates to methods of regulating hair growth using a safe and effective amount of hexamidine, cetyl pyridinium chloride, ursolic acid or BHT, their salts and derivatives; and a dermatologically acceptable carrier for any of the compounds.

The present invention also relates to methods of regulating hair growth using a safe and effective amount of BHT or BHA; a safe and effective amount of an additional skin care active selected from the group consisting of hexamidine, cetyl pyridinium chloride, phytosterol, green tea catechins, and ursolic acid, their salts and derivatives, and mixtures thereof; and a dermatologically acceptable carrier for the BHT compound.

The present invention also relates to methods of regulating hair growth using a safe and effective amount of hexamidine; a safe and effective amount of an additional skin care active selected from the group consisting of cetyl pyridinium chloride, phytosterol, green tea catechins, and ursolic acid, their salts and derivatives, and mixtures thereof; and a dermatologically acceptable carrier for the hexamidine compound.

The present invention also relates to methods of regulating hair growth using a safe and effective amount of cetyl pyridinium chloride; a safe and effective amount of an additional skin care active selected from the group consisting of phytosterol, green tea catechins, and ursolic acid, their salts and derivatives, and mixtures thereof; and a dermatologically acceptable carrier for the cetyl pyridinium chloride compound.

The present invention also relates to methods of regulating hair growth using a safe and effective amount of phytosterol; a safe and effective amount of an additional skin care active selected from the group consisting of green tea catechins and ursolic acid, their salts and derivatives, and mixtures thereof; and a dermatologically acceptable carrier for the BHT compound.

The present invention also relates to methods of regulating hair growth using a safe and effective amount of green tea catechins and a safe and effective amount of ursolic acid, their salts and derivatives, and mixtures thereof; and a dermatologically acceptable carrier for the green tea catechin compound.

These and other features, aspects, and advantages of the present invention will become evident to those skilled in the art from a reading of the present disclosure.

DETAILED DESCRIPTION

While the specification concludes with the claims particularly pointing and distinctly claiming the invention, it is believed that the present invention will be better understood from the following description.

The compositions of the present invention can include, consist essentially of, or consist of, the components of the present invention as well as other ingredients described herein. As used herein, "consisting essentially of" means that the composition or component may include additional ingredients, but only if the additional ingredients do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore, do not include carriers or by-products that may be included in commercially available materials, unless otherwise specified.

All publications cited herein are hereby incorporated by reference in their entirety.

As used herein, the "beauty care products" are those used to treat or care for, or somehow moisturize, improve, or clean the skin and/or hair. Products contemplated by the phrase "beauty care products" include, but are not limited to moisturizers, personal cleansing products, occlusive drug delivery patches, powders, wipes, hair conditioners, hair tonics, shampoos, hair colorants, skin treatment emulsions, shaving creams, antiperspirants, deodorants, and the like.

The compositions of the present invention are useful for regulating the growth of mammalian hair. Hair growth regulation is often desired in certain parts of the body due to hygiene or societal pressures. The desire for hair growth regulation may also stem from hair growth patterns induced or caused by factors internal and/or external to the body. Examples include, environmental damage, radiation exposure (including ultraviolet radiation and radiation therapy), heredity, chronological aging, menopausal status (e.g., post-menopausal changes in hair growth), stress, diseases, chemotherapy, etc.

"Regulating hair growth," namely mammalian hair growth, includes reducing, modulating, inhibiting, attenuating, retarding, promoting, enhancing, and/or the diminuation of hair growth, and/or reducing shaving frequency.

"Reduction/Inhibition of hair growth," as referenced herein, is demonstrated when the frequency of hair removal is reduced, or the tactile and visual feel of mammalian hair is improved wherein the subject perceives less hair on the treated site (i.e., hair is perceived to be softer, finer, less noticeable), or quantitatively, when the weight of the hair removed by shaving (i.e., hair mass) is reduced thereby improving the ease, frequency, and effectiveness of shaving of a mammal.

"Mammalian hair," as referenced herein, includes hair on any part of the body of a mammal and may include facial, cranial, or body hair. Male facial hair commonly refers to the beard, moustache, eyebrows and sideburns hair, but may include any area of the face and/or neck. Female facial hair (predominantly vellus but can include terminal hair) commonly refers to eyebrows, upper lip, chin, and cheeks area, but may also include any area of the face and/or neck. Other areas of hair growth typically desired to be regulated include underarms, bikini area, legs, arms, back, and chest. The desire for hair loss reduction is frequently associated with cranial hair, especially cranial hair in chemotherapy and/or radiation therapy patients. The compositions of the present invention are particularly suitable for reducing the growth of unwanted hair in women suffering from hirsutism or other conditions.

The composition is particularly suitable for the treatment of hirsutism. In humans, the composition should be applied once or twice a day, or even more frequently, for at least three months to achieve a perceived reduction in hair growth.

The term "improving the tactile and visual feel" as used herein, refers to the more noticeable improvement in the appearance of the hair on the skin such that it is perceived to be softer, finer, less noticeable. Additionally, the ease, frequency, and effectiveness of shaving will be perceived by the mammal. Reduction of hair growth is demonstrated when the frequency of hair removal is reduced, or the subject perceives less hair on the treated site, or quantitatively, when the weight of hair removed by shaving (i.e., hair mass) is reduced.

The term "keratinous tissue," as used herein, refers to keratin-containing layers disposed as the outermost protective covering of mammals (e.g., humans, dogs, cats, etc.) which includes, but is not limited to, skin, hair, etc.

The term "topical application", as used herein, means to apply or spread the compositions of the present invention onto the surface of the keratinous tissue.

The term "dermatologically-acceptable," as used herein, means that the compositions or components thereof so described are suitable for use in contact with mammalian keratinous tissue without undue toxicity, incompatibility, instability, allergic response, and the like.

The term "safe and effective amount" as used herein means an amount of a compound or composition sufficient to significantly induce a positive benefit, preferably a hair growth regulating benefit, or positive hair appearance or feel benefit, including independently or in combinations the benefits disclosed herein, but low enough to avoid serious side effects, i.e., to provide a reasonable benefit to risk ratio, within the scope of sound judgment of the skilled artisan. The term "ambient conditions" as used herein refers to surrounding conditions under about one atmosphere of pressure, at about 50% relative humidity, and at about 25° C. unless otherwise specified. The compositions of the present invention provide additional benefits, including stability, absence of significant (consumer-unacceptable) skin irritation and good aesthetics.

The compositions of the present invention are stable. The ingredients used herein, including the agmatine, are compatible with each other and with the other skin care actives such as terpene alcohols, retinoids, peptides, tocopherol sorbate, and vitamin $B_3$ compounds. Therefore, the compositions containing the combination of agmatine in conjunction with an additional skin care active, such as hexamidine, cetyl pyridinium chloride, phytosterols, BHT, BHA, compounds derived from plant extracts, green tea catechin compounds, ursolic acid, and free fatty acids, are capable of providing additive and/or synergistic skin benefits. Additionally, the resulting skin care composition has good product stability and a reasonably long shelf-life.

The resulting compositions containing agmatine in combination with other selected skin care actives have good aesthetics. Examples of good aesthetics include compositions, such as luxurious creams and lotions, that (i) are light and nongreasy, (ii) have a smooth, silky feel upon the skin, (iii) spread easily, and/or (iv) absorb quickly. Other examples of good aesthetics include compositions that have a consumer acceptable appearance (i.e. no unpleasant odor or discoloration present), and provide good skin feel. The compositions herein may include a wide variety of other optional ingredients.

The compositions of the present invention, including the essential and optional components thereof, are described in detail hereinafter.

I. Materials

A. Agmatine

The topical composition of the present invention comprises a safe and effective amount of agmatine. The agmatine useful herein can be described by the general structure:

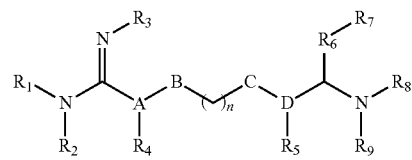

$R_1$, $R_2$, $R_3$, $R_4$, $R_5$, $R_6$, $R_7$, $R_8$, $R_9$=alkyl, cycloalkyl, heteroalkyl, heterocycloalkyl, aromatic, heteroaromatic, carboxamido, sulfonamido, carboxyl, carboxylate, carbamate, urea, sulfate, phosphate, silyl, acyl, amino acid, polypeptide, imino, hydrogen, nitro, nitrogen, oxygen, sulfur, phosphorus, nil.

A, D=carbon, nitrogen, aromatic, heteroaromatic, hydrogen, nil.

B, C=nitrogen, oxygen, sulfur, phosphorus, hydrogen, nil.

n=0 to 20.

In the composition of the present invention, agmatine preferably comprises from about 0.0001% to about 99.99% by weight of the composition, more preferably from about 0.001% to about 10%, more preferably from about 0.01% to about 5%, and most preferably from about 0.1% to about 2.5%.

B. Skin Care Actives

The topical composition of the present invention includes a first additional skin care active selected from the group consisting of BHT or BHA, hexamidine, cetyl pyridinium chloride, green tea catechins, phytosterols, ursolic acid, and their salts and derivatives.

The topical composition of the present invention also includes a second additional skin care active selected from the group consisting of BHT or BHA, hexamidine, cetyl pyridinium chloride, green tea catechins, phytosterols, ursolic acid, and their salts and derivatives, and mixtures thereof, wherein the second additional skin care active is different from the first skin care active.

1. Butylated Hydroxytoluene (BHT) and Butylated Hydroxyanisole (BHA)

The topical compositions of the present invention comprise a safe and effective amount of BHT or BHA. The BHT useful herein can be described by the general structure:

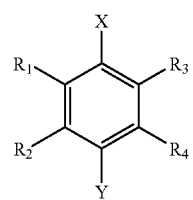

X=OH, SH

Y=H, OH, $OR_5$, $COOR_5$, alkyl, cycloalkyl, heteroalkyl, heterocycloalkyl, aromatic, heteroaromatic, carboxamido, sulfonamido, carbamate, urea, trialkylsilyl $R_1$, $R_2$, $R_3$, $R_4$=alkyl, cycloalkyl, heteroalkyl, heterocycloalkyl, aromatic, heteroaromatic, $OR_5$, carboxamido, sulfonamido, formyl, acyl, carboxyl, carboxylate, carbamate, urea, trialkylsilyl, hydroxyl, hydrogen $R_5$=alkyl, cycloalkyl, heteroalkyl, heterocycloalkyl, aromatic, heteroaromatic, trialkylsilyl, acyl, hydrogen.

In the composition of the present invention, BHT or BHA preferably comprises from about 0.0001% to about 99.99% by weight of the composition, more preferably from about 0.001% to about 10%, more preferably from about 0.01% to about 5%, and most preferably from about 0.1% to about 0.5%.

2. Hexamidine

The topical composition of the present invention comprises a safe and effective amount of hexamidine, its salt, and derivatives. More preferably, the hexamidine is hexamidine isethionate. As used herein, "hexamidine" includes any isomers and tautomers of such and is commercially available as hexamidine isethionate under the tradename Elastab® HP100 from Laboratoires Serobiologiques (Pulnoy, France).

In the composition of the present invention, hexamidine preferably comprises from about 0.0001% to about 99.99% by weight of the composition, more preferably from about 0.001% to about 10%, more preferably from about 0.01% to about 5%, and most preferably from about 0.1% to about 2.0%.

3. Cetyl Pyridinium Chloride

The topical composition of the present invention comprises a safe and effective amount of cetyl pyridinium chloride. Alternate forms of cetyl pyridinium chloride include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphenbromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium agents. Other compounds are bis)4-(R-amino)-1-pyridinium! alkanes as disclosed in U.S. Pat. No. 4,206,215, Jun. 3, 1980 to Bailey which is incorporated herein by reference. The pyridinium compounds are the preferred quaternary ammonium compounds for use in the present invention, the most preferred being cetyl pyridinium chloride.

In the composition of the present invention, cetyl pyridinium chloride preferably comprises from about 0.0001% to about 99.99% by weight of the composition, more preferably from about 0.001% to about 5%, more preferably from about 0.01% to about 2%, and most preferably from about 0.05% to about 1.0%.

4. Green Tea Catechins

The topical composition of the present invention comprises a safe and effective amount of one or more catechin compounds selected from the group consisting of catechin, epicatechin, epigallocatechin, epicatechin gallate, epigallocatechin gallate, gallocatechin, and mixtures thereof. More preferably, the catechin is free of caffeine and is extracted and enriched for from a green tea plant source. Most preferably, the catechin is epigallocatechin gallate.

In the composition of the present invention, the catechin mixture preferably comprises from about 0.0001% to about 99.99%, by weight of the composition, more preferably from about 0.001% to about 10%, more preferably from about 0.01% to about 5%, and most preferably from about 0.1% to about 2.5%, by weight of the composition.

5. Phytosterols

The topical composition of the present invention comprises a safe and effective amount of one or more phytosterols selected from the group consisting of β-sitosterol, campesterol, brassicasterol, Δ5-avennasterol, lupenol, α-spinasterol, stigmasterol, their derivatives, and combinations thereof. More preferably, the phytosterol is selected from the group consisting of β-sitosterol, campesterol, brassicasterol, stigmasterol, their derivatives, and combinations thereof. Even more preferably, the phytosterol is selected from the group consisting of β-sitosterol, campesterol, brassicasterol, stigmasterol, and combinations thereof. Most preferably, the phytosterol is stigmasterol.

Phytosterols of the present invention can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers, tautomers, and derivatives (e.g., esters) of such and are commercially available from Aldrich Chemical Company (Milwaukee, Wis.), Sigma Chemical Company (St. Louis, Mo.), Cognis, and Karlshamns (Karlshamns, Sweden).

In the compositions of the present invention, the phytosterol preferably comprises from about 0.01% to about 99.99%, by weight of the composition, more preferably from about 0.01% to about 50%, even more preferably from about 0.1% to about 20%, still more preferably from about 0.2% to about 10%, and most preferably from about 0.5% to about 10%.

6. Ursolic Acid

The topical composition of the present invention comprises a safe and effective amount of ursolic acid. In the composition of the present invention, the ursolic acid preferably comprises from about 0.0001% to about 99.99% by weight of the composition, more preferably from about 0.001% to about 10%, more preferably from about 0.01% to about 5%, and most preferably from about 0.05% to about 5%.

7. Compounds Derived from Plant Extracts

The topical compositions of the present invention comprise a safe and effective amount of compounds derived from plant extracts selected from the group consisting of leguminosae, solanaceae, gramineae, cucurbitaceae. Preferably, the compound derived from plant extracts is a protease inhibitor and one or more isoflavone. In the composition of the present invention, compounds derived from plant extracts preferably comprises from about 0.0001% to about 99.99% by weight of the composition, more preferably from about 0.001% to about 10%, more preferably from about 0.01% to about 5%, and most preferably from about 0.05% to about 5%.

C. Dermatologically Acceptable Carrier

The topical compositions of the present invention also comprise a dermatologically acceptable carrier for the catechin composition. The phrase "dermatologically acceptable carrier", as used herein, means that the carrier is suitable for topical application to the keratinous tissue, has good aesthetic properties, is compatible with the actives of the present invention and any other components, and will not cause any safety or toxicity concerns. A safe and effective amount of carrier is from about 50% to about 99.99%, preferably from about 60% to about 99.9%, more preferably from about 70% to about 98%, and most preferably from about 80% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers comprise an emulsion such as oil-in-water emulsions and water-in-oil emulsions, e.g., silicone-inwater or water-in-silicone emulsions. As will be understood by the skilled artisan, a given component will distribute primarily into either the water or oil phase, depending on the water solubility/dispensability of the component in the composition. The catechin compound distributes primarily into the oil phase. Oil-in-water emulsions are especially preferred.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the composition. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers*, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less.

Preferred water-in-silicone and oil-in-water emulsions are described in greater detail below.

1) Water-in-Silicone Emulsion

Water-in-silicone emulsions contain a continuous silicone phase and a dispersed aqueous phase.

(a) Continuous Silicone Phase

Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase contains a polyorganosiloxane oil. A preferred water-in-silicone emulsion system is formulated to provide an oxidatively stable vehicle for an optional retinoid. The continuous silicone phase of these preferred emulsions comprises between about 50% and about 99.9% by weight of organopolysiloxane oil and less than about 50% by weight of a non-silicone oil. In a preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These preferred emulsion systems provide more oxidative stability to a retinoid over extended periods of time than comparable water-in-oil emulsions containing lower concentrations of the polyorganosiloxane oil. Concentrations of non-silicone oils in the continuous silicone phase are minimized or avoided altogether so as to further enhance oxidative stability of the selected retinoid in the compositions. Water-in-silicone emulsions of this type are described in copending U.S. patent application Ser. No. 08/570,275, filed Dec. 11, 1995, in the names of Joseph Michael Zukowski, Brent William Mason, Larry Richard Robinson and Greg George Hillebrand.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Concentrations of non-silicone oils in the continuous silicone phase are preferably minimized or avoided altogether so as to further enhance oxidative stability of any retinoids in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

(b) Dispersed Aqueous Phase

The topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention will typically comprise from about 25% to about 90%, preferably from about 40% to about 80%, more preferably from about 60% to about 80%, water in the dispersed aqueous phase by weight of the composition.

(c) Emulsifier for Dispersing the Aqueous Phase

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and most preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethylsiloxanes that have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds that contain C2-C30 pendant side chains. Still other useful dimethicone copolyols include materials having various cationic, anionic, amphoteric, and zwitterionic pendant moieties.

The dimethicone copolyol emulsifiers useful herein can be described by the following general structure:

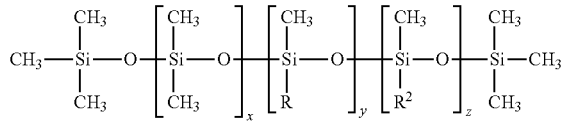

wherein R is C1-C30 straight, branched, or cyclic alkyl and $R^2$ is selected from the group consisting of

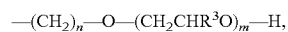

and

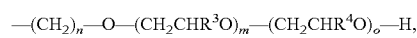

wherein n is an integer from 3 to about 10; $R^3$ and $R^4$ are selected from the group consisting of H and C1-C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

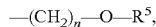

$$—(CH_2)_n—O—R^5,$$

wherein $R^5$ is a cationic, anionic, amphoteric, or zwitterionic moiety.

Dimethicone copolyol emulsifiers useful herein are described, for example, in U.S. Pat. No. 4,960,764, to Figueroa, Jr. et al., issued Oct. 2, 1990; European Patent No. EP 330,369, to Sanogueira, published Aug. 30, 1989; G. H. Dahms, et al., "New Formulation Possibilities Offered by Silicone Copolyols," *Cosmetics & Toiletries*, vol. 110, pp. 91-100, March 1995; M. E. Carlotti et al., "Optimization of W/O—S Emulsions And Study Of The Quantitative Relationships Between Ester Structure And Emulsion Properties," *J. Dispersion Science And Technology*, 13(3), 315-336 (1992); P. Hameyer, "Comparative Technological Investigations of Organic and Organo silicone Emulsifiers in Cosmetic Water-in-Oil Emulsion Preparations," HAPPI 28(4), pp. 88-128 (1991); J. Smid-Korbar et al., "Efficiency and usability of silicone surfactants in emulsions," *Provisional Communication, International Journal of Cosmetic Science*, 12, 135-139 (1990); and D. G. Krzysik et al., "A New Silicone Emulsifier For Water-in-Oil Systems," *Drug and Cosmetic Industry*, vol. 146(4), pp. 28-81 (April 1990).

Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

2) Oil-in-Water Emulsions

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371, to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

(a) Structuring Agent

A preferred oil-in-water emulsion comprises a structuring agent to assist in the formation of a liquid crystalline gel network structure. Without being limited by theory, it is believed that the structuring agent assists in providing rheological characteristics to the composition that contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, steareth-21, and mixtures thereof.

(b) Hydrophilic Surfactant

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the composition). The surfactant, at a minimum, must be hydrophilic enough to disperse in water.

Suitable surfactants include any of a wide variety of known cationic, anionic, zwitterionic, and amphoteric surfactants. See, *McCutcheon's, Detergents and Emulsifiers*, North American Edition (1986), published by Allured Publishing Corporation; U.S. Pat. No. 5,011,681; U.S. Pat. No. 4,421, 769; and U.S. Pat. No. 3,755,560; these references are incorporated herein by reference in their entirety.

The exact surfactant chosen will depend upon the pH of the composition and the other components present.

Preferred are cationic surfactants, especially dialkyl quaternary ammonium compounds, examples of which are described in U.S. Pat. No. 5,151,209; U.S. Pat. No. 5,151, 210; U.S. Pat. No. 5,120,532; U.S. Pat. No. 4,387,090; U.S. Pat. No. 3,155,591; U.S. Pat. No. 3,929,678; U.S. Pat. No. 3,959,461; *McCutcheon's, Detergents & Emulsifiers, (North American edition* 1979) M. C. Publishing Co.; and Schwartz, et al., *Surface Active Agents, Their Chemistry and Technology*, New York: Interscience Publishers, 1949; which descriptions are incorporated herein by reference.

A wide variety of anionic surfactants are also useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO—OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine.

Another suitable class of anionic surfactants is the water-soluble salts of the organic, sulfuric acid reaction products of the general formula:

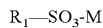

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and β-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_mCO_2M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, or alkanolammonium. Also included are imidazolinium and ammonium derivatives. Other examples of useful amphoterics include phosphates, such as coamidopropyl PG-dimonium chloride phosphate (commercially available as Monaquat PTC, from Mona Corp.).

Also useful herein as amphoteric or zwitterionic surfactants are the betaines, sultaines and hydroxysultaines such as cocamidopropyl hydroxysultaine (available as Miratame CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

(c) Water

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water insoluble or partially soluble materials such as are known in the art, including but not limited to the silicones described herein in reference to silicone-in-water emulsions, and other oils and lipids such as described above in reference to emulsions.

(d) Composition Forms

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology*, 2nd Edition, Vol. 1, pp. 32-43 (1972), incorporated herein by reference, contains numerous examples of materials suitable as an emollient. A preferred emollient is glycerin. Glycerin is preferably used in an amount of from about 0.001% to about 20%, more preferably from about 0.01% to about 10%, and most preferably from about 0.1% to about 7%, e.g., 5%.

Lotions and creams according to the present invention generally comprise a solution carrier system and one or more emollients. Lotions typically comprise from about 1% to about 20%, preferably from about 5% to about 10%, of emollient; from about 50% to about 90%, preferably from about 60% to about 80%, water; and the catechin in the above described amounts. A cream typically comprises from about 5% to about 50%, preferably from about 10% to about 20%, of emollient; from about 45% to about 85%, preferably from about 50% to about 75%, water; and the catechin in the above described amounts.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics Science and Technology*, 2nd Edition, Vol. 1, pp. 72-73 (1972), incorporated herein by reference, and/or an emollient.

Compositions of this invention useful for cleansing ("cleansers") are formulated with a suitable carrier, e.g., as described above, and preferably contain, in addition to the catechin in the above described amounts and from about 1% to about 90% of a dermatologically acceptable surfactant.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989.

The compositions of the present invention may also be in the form of cosmetics. Suitable cosmetic forms include, but are not limited to, foundations, lipsticks, rouges, mascaras, and the like. Such cosmetic products may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter.

D. Optional Components

The compositions of the present invention may contain a variety of other ingredients that are conventionally used in given product types provided that they do not unacceptably alter the benefits of the invention.

The optional components, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

1.) Hair Growth Inhibiting Compounds

The compositions of the present invention may also comprise other hair growth inhibiting compounds. These compounds are known in the art as inhibiting hair growth and consist of the following: 1,10-phenanthroline; 5'-p-fluorosulphonyl benzoyl adenosine; 5-keto-D-fructose; 5-keto-D-fructose-1,6-bisphosphate; 6-amino-6-deoxyglucose; agaric acid; Br-cAMP; cysteine sulphinic acid; D-mannosamine; diethylaminomalonate; doxycycline; ethacrynic acid; ethoxyquin; eupacunin; euparotin acetate; fluvastatin; guanidino succinic acid; inhibitor of a cysteine pathway enzyme; methacycline; mevastatin; mevinolin; minocycline; N-alpha-(p-tosyl)-L-lysine chloromethyl ketone; N-acetyl-beta-D-mannosamine; oxaloacetic acid; phosphoglycerate; pravastatin; protocatechuic aldehyde; quinaldic acid; rivastatin; simvastatin; squalestatin; taxodione; taxodone; tetracycline; vernolepin; 1,10-phenanthroline; 1,8-diaminooctane; 2-methyl-6-heptyne-2,5-diamine; 3-carboxypropyl disulphide; saw palmetto extract, willow herb extract, pumpkin seed extract, 5-(N-benzyloxycarbonyl)-1-phenylalanamidomethyl)-3-bromo-4,5-dihydroisoxazole; 5'-deoxy-5'-(N-methyl-N-(2-aminooxy-ethyl)-aminoadenosine (MAOEA); 5'-deoxy-5'-methyl-thioadenosine; 6-heptyne-2,4-diamine; actinonin; alpha-methyl-DL-methionine; alpha-ethyl-ornithine; apigenin; arginase inhibitor; batimistat; Br-cAMP; caffeic acid; captopril; chlorotaurine; cholesterol pathway enzyme inhibitor; cyclooxygenase inhibitor; cysteamine; cysteine sulphinic acid; cysteinyl-glycine; D-cysteine; D-penicillamine; difluoromethylornithine (DFMO); diethyl aminomalonate; diethyl glyoxal bis(quanylhydrazone); diethyldithiocarbamic acid; dimethyl cysteamine; doxycycline; eicosapentaenoic acid; estramustine; ethacrynic acid; etoposide; guanidino succinic acid; H-homoarginine; inhibitor of a cholesterol pathway enzyme; inhibitor of the formation of glycoproteins, proteoglycans or glycosaminoglycans; inhibitor of the hypusine biosynthetic pathway; L-alanosine; L-argininamide; L-asparaginamide; L-cysteine methyl ester; lipoic acid; lovastatin; marimistat; matlystatin-B; meso-dimercaptosuccinic acid; methacycline; methylglyoxal bis(guanylhydrazone); minocycline; N(G)-methyl-L-arginine; N—[N[((R)-1-phosphonopropyl)-(S)-leucyl]-(S)-phenylalanine-N-methylamide; N-acetylcysteine; N-phosphonalkyl dipeptides; N-phosphonoacetyl-aspartic acid; nalidixic acid; N-alpha-acetyl-L-arginine; N-alpha-benzoyl-L-argininamide; N-alpha-benzoyl-L-arginine; N-alpha-benzoyl-L-arginine methyl ester; NG-L-arginine benzyl ester; NG-nitro-L-arginine; NG-nitro-L-arginine methyl ester; nordihydroguaianetic acid (NDGA); extract from creosote; oxaloacetic acid; pantothenic acid; pantothenic acid analogues; phosphocysteamine; propyl gallate; protein kinase C inhibitor; protocatechuic aldehyde; protocatechuic aldehyde; quercetin; S-carbamyl-L-cysteine; S-trityl-L-cysteine; sulphasalazine; suppressor of angiogenesis; tetracycline; thiosalicylic acid; tyramine; 2-difluoromethyl-, 2,5-diamino pentanoic acid; herbimycin; HNMPA (AM)3; inhibitor of alkaline phosphatase; lavendustin A; methyl caffeate; protein-tyrosine kinase inhibitors; Tryphostin A47; O-p-nitrohydroxylamine, alpha.-fluoromethylhistidine, mycophenolic acid, bromocryptine, cromoglycate, quinoline-3-carboxamide, 16 alpha- or beta-substituted 4-aza-5 alpha-androst-1-en-3-ones; 2-aryl-indole derivatives; 2-phenyl-3-aminoalkyl-indole derivatives; 3-oxo-4-aza-5 alpha-androstane derivs; 5 alpha-androstan-3-ones; 5-(aminocarbonylalkyl)-3-(heterobicyclyl-alkylaminoalkyl)-2-phenylindole derivatives; 6-azaindole derivatives; 7-azaindole derivatives; aryl-imidazopyridines; finasteride; GnRH inhibitors, aloe; carboxyalkylamine derivatives; clove; *Echinacea angustifolia; Echinacea purpurea*; elasatin decomposition enzyme inhibitor; extracts from ginger; hydrolyzing almond; *Lithosperumum*; peptides; extract of *Rosaceae*; extract of *Sanguisorba officinalis; Tropaeolum majus*; extract of white birch and *rubiaceae* plant groups; extract of *Juniperus* genus and/or malt extract; malonamide derivatives; elastase inhibitor; papain, trypsin, chymotrypsin, pepsin, bromelain, ficin or pancreatin; plant fruit enzyme extracts; compounds from *Pleione* sp., *Curcuma longa* L. or *Diopyros kaki*; 2-indole carboxylic acid derivatives; alpha-TNF antagonist; amino-propanes; bacterium ribosomes; non-steroidal anti-inflammatory drugs (NSAIDS); diethylenediamines; histamine antagonist; interleukin-1 antagonist; lipoxygenase inhibitors and stimulants; phenothiazines; sulfotransferase inhibitors; tetrazolylbenzofuran carboxamides; tetrazolyl-benzothiophene carboxamides; cyanoguanidine derivatives; 17alpha-hydroxy-4,9(11)-pregnadiene-3,20-dione derivatives; anti-angiogenic steroids; pyrimidine-cyanoguanidine derivs; substd. amidine or guanidine. benzothiophene derivatives; (−)cis 6(S)-phenyl-5(R)-[4-(2-pyrrolidin-1-ylethoxyphenyl]-5,6,7,8-tetrahydronaphthelen-2-ol D-tartrate (I); tetrahydronaphthalene derivatives; estrogen agonists or antagonists; tetrahydroisoquinolines; Heptapeptide luteinizing hormone releasing hormone (LHRH) analogs; tetrahydroisoquinoline derivatives; tetrahydroisoquinoline derivatives; 3-(anilinomethylene) oxindole derivatives; benzo-[f]-quinolin-3-one derivative; ((S-(−)-N-(alpha-ethylbenzyl)-3-hydroxy-2-phenylquinoline-4-carboxamide); 24-ethyl-(Delta)4,22-cholestadien-3-one; extracts from *Hydrangea macrophylla; Hydrangea serrata; Iridaceae Belamcanda Adans; Iridaceae Iris L.; Moraceae Humulus*; CDK binding proteins; chimeric polypeptide with cyclin-dependent kinase (CDK) binding motif; E6AP-binding polypeptides; 2-mercaptoethanol; 2-mercaptopropionic acid; cysteine; diethyldithiocarbamic acid; dithiothreitol; glutathione; homocysteine; lipoic acid; mecaptopropionic acid; N-acetyl-L-cysteine; thiodiglycol; thiodiglycolic acid; thioglycerol; thioglycolic acid; thiolactic acid; thiomalic acid; thiopropionic acid; thiosalicylic acid; thioxanthine; benzoic acid lactone ether; 1-halomethyl-5alpha-androstanes and delta-androsteness; hedgehog antagonists; patched antagonists; copper; iron; zinc; 1 dehydromelengestrol acetate; 1-dehydromegestrol acetate; chlormadinone acetate; cyproterone acetate; medroxyprogesterone acetate; megestrol acetate; melengestrol acetate; nomegestrol acetate; non-elastomeric polyolefin resin; partially fluorinated polyolefin resin; nucleic acid molecule; trypsin analogs; bacteriostatic or haemostyptic agent, especially stannous fluoride; alpha- or gamma-linolenic acid; EGF; lipoxygenases; extract of Regulo plant (*Abelmoschus moschatus*); extract of Wolo plant (*Borassus flabellifer*); androstenedione analogues; activin A (polypeptide); hydrindanes; butyric acid derivatives; phytoestrogen; Tetrahydroisoquinolines; tetrahydronaphthalenes; 3-amino-2,3-dihydro benzoic acid; 6-fluoro-2,5-diamino hexanoic acid; (S)-2-amino-4-amino oxy-butyric acid; extracts of fruits and other plant parts from *Serenoa repens*; carrot oil; clove oil; diazo compounds; essential oil; honey; juniper oil; lavender oil; lemon juice; palmarosa oil; rosemary oil; sugar; sugary substance; thuja oil; triarylmethane compounds; Perfluoro-substituted aniline derivatives; 17alpha-propyltestosterone; 4-androstene-3-one 17beta-carboxylic acid; (4R)-5,10-seco-19-norpregna 4,5-diene-3,10,20-trione; chlormadinone acetate; cyproterone acetate; progesterone; spironolactone; melatonin; Bowman Birk inhibitor (soy derived); 2-substd. 6-tetra hydronaphthyl or indanyl naphthalene derives; aqueous alcoholic extract from genus *Centipeda*; antagonist of the hedgehog signal transduction pathway; epidermal growth factor (EGF); finasteride; spironolactone; fatty acids; 2-phenyl-benzothiophene derivs.; 2-arylimino-oxaza or thiaza heterocyclic compounds; glutathione synthesis stimulators; indole derivatives; *Cinnamonum verum; Curcurbita pepo; Epilobium roseum; Salvia officinalis; Serenoa repens; Cassia obtusifoila Linne*; polynucleotide; dormant cell extracts; N-substituted. benzyl- or thienylmethyl-4-pyridone cpds; (1H)-benzo(c)quinolizin-3-one derivatives; 5-alpha-reductase inhibitors; adenylsuccinate synthetase inhibitor; aspartate transcarbamylase inhibitor; gammaglutamyl transpeptidase inhibitor; Ornithine decarboxylase inhibitors; citric acid; Dead Sea salt; visaborol; ant eggs; androgen receptor blockers; previtamin D; provitamin D; vitamin D; vitamin K; *Cucurbitaceae*; extract of Ikurinin; phosphodiesterase; Phlondrin; phloretin; 5 alpha-androstene-3 alpha,17 beta-diol; cyproterone; *Hedera helex; Lithospermum* root; medoroxyprogesterone; mestanolone; norethisterone; *Scutellaria* root; tomato; extract of *Commiphora myrrha; Cymbopogon nardus; Lagerstroemia speciosa; phyllanthus nuriri; Smilax zeylanica; Woodfordia fruticosa*; chelating agents; chlorophenol; o-phenylphenol; phenol; Niphtolide; peach oil; sorbic acid; *Cistanche salsa; Plantago asiatica* L.; *Stachys sieboldii*; 2-amino-5-substd. benzophenone; Aniline derives; bur marigold infusion; camphor oil; citric acid; conifer extract; daisy infusion; honey; sea-buckthorn oil; tannin solution; capsicum; capsicum extract (Solanaceae family); conjugate comprising active agent substituted with amino acid, peptide or trisamine carrying fatty acid ester and dithioalkanoyl groups; recombinant DNA encoding EGF; recombinant DNA encoding TGFalpha; 11-beta-aryl-17-spiropyrrolin-2-ylidene N-oxide steroid progestins and antiprogestins; phenyl imidazolidines; ammonium salt of weak acids; essential oils; vitamin F; Coumarin derivatives; leuteinizing hormone-releasing hormone; leuteinizing hormone-releasing hormone analogs; Hydroxamic acid derivatives; bomeol; cineole; linalol; methyl heptenone; oil of ginger; shogaol; zingerone; zingiberol; zingiberone; glutathione S-transferase modulator; aminoacid(s); lipoxydase; inhibitor of glutamine metabolism; thiomolybdate compound; Hairless protein inhibitor; aromatase inhibitor; trifluoroanilide derivatives; EGF; EGF analogues; and extract of seeds of *Coix lachryma-jobi*.

2.) Depilatories

Certain embodiments of the present invention may optionally contain a depilatory. As used herein, "depilatory" means an agent capable of removing hair from the skin by cleaving the disulfide bonds in hair keratin, thereby causing the hair fiber to disintegrate. Preferred depilatories useful in the subject invention include ammonium thioglycolate, barium sulfate, calcium thioglycolate, ethanolamine thioglycolate, potassium thioglycolate, sodium thioglycolate, thioglycolic acid and thioacetic acid. When present in the composition, the composition contains from about 0.0001_% to about 99.9_%, preferably from about 0.001% to about 10%, and more preferably from about 0.01% to about 5%, by weight of the composition, of the depilatory. Examples of suitable depilatories are described in further detail in U.S. Pat. No. 5,897,857.

3.) Desquamation Actives

A safe and effective amount of a desquamation active may be added to the compositions of the present invention, more preferably from about 0.01% to about 10%, even more preferably from about 0.5% to about 5%, also preferably from about 0.1% to about 2%, by weight of the composition. Desquamation actives enhance the skin appearance benefits of the present invention. For example, the desquamation actives tend to improve the texture of the skin (e.g., smoothness). One desquamation system that is suitable for use herein comprises sulflhydryl compounds and zwitterionic surfactants and is described in U.S. Pat. No. 5,681,852, issued on Oct. 28, 1997, in the name of Donald L. Bissett, corresponding to WO 96/01101, published on Jan. 18, 1996. Another desquamation system that is suitable for use herein comprises salicylic acid and zwitterionic surfactants and is described in U.S. Pat. No. 5,652,228, issued on Jul. 29, 1997, as a continuation of Ser. No. 08/209,041, filed on Mar. 9, 1994, now abandoned, in the name of Bissett, corresponding to WO95/13048, published on May 18, 1995. Zwitterionic surfactants such as described in these applications are also useful as desquamatory agents herein, with cetyl betaine being particularly preferred.

4.) Anti-Acne

The compositions of the present invention may comprise a safe and effective amount of one or more anti-acne actives. Examples of useful anti-acne actives include resorcinol, sulfur, salicylic acid, erythromycin, zinc, etc. Further examples of suitable anti-acne actives are described in further detail in U.S. Pat. No. 5,607,980, issued to McAtee et al., on Mar. 4, 1997.

5.) Anti-Wrinkle Actives/Anti-Atrophy Actives

The compositions of the present invention may further comprise a safe and effective amount of one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol; hydroxy acids (e.g., salicylic acid, glycolic acid), keto acids (e.g., pyruvic acid), ascorbic acid (vitamin C), phytic acid, lipoic acid; lysophosphatidic acid, skin peel agents (e.g., phenol and the like), flavonoids (e.g., flavanones, chalcones, isoflavones, flavones, etc.), stilbenes, cinnamates, resveratrol, kinetin, zeatin, dimethylaminoethanol, peptides from natural sources (e.g., soy peptides), salts of sugar acids (e.g., Mn gluconate), terpene alcohols (e.g., farnesol), peptides, vitamin $B_3$ compounds and retinoids which enhance the keratinous tissue appearance benefits of the present invention, especially in regulating keratinous tissue condition, e.g., skin condition, and other vitamin B compounds (e.g., thiamine (vitamin B1), pantothenic acid (vitamin B5), carnitine (vitamin Bt), riboflavin (vitamin B2), cobalamine (vitamin B12), pangamic acid or diisopropylamine dichloroacetate (vitamin B15's), and their derivatives and salts (e.g., HCl salts or calcium salts)).

(a) Vitamin $B_3$ Compounds

The compositions of the present invention may comprise a safe and effective amount of a vitamin $B_3$ compound. Vitamin $B_3$ compounds are particularly useful for regulating skin condition as described in co-pending U.S. application Ser. No.

08/834,010, filed Apr. 11, 1997 (corresponding to international publication WO 97/39733 A1, published Oct. 30, 1997). When vitamin $B_3$ compounds are present in the compositions of the instant invention, the compositions preferably comprise from about 0.01% to about 50%, more preferably from about 0.1% to about 10%, even more preferably from about 0.5% to about 10%, and still more preferably from about 1% to about 5%, most preferably from about 2% to about 5%, by weight of the composition, of the vitamin $B_3$ compound.

(b) Retinoids

The compositions of the present invention may also comprise a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters (saturated or unsaturated alkyl chains) of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Preferred retinoids are retinol, retinyl palmitate, retinyl acetate, retinyl propionate, retinal and combinations thereof.

(c) Anti-Oxidants/Radical Scavengers

The compositions of the present invention may include a safe and effective amount of an anti-oxidant/radical scavenger. The anti-oxidant/radical scavenger is especially useful for providing protection against UV radiation that can cause increased scaling or texture changes in the stratum corneum and against other environmental agents, which can cause skin damage.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee.

(d) Chelators

The compositions of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime and derivatives.

(e) Flavonoids

The compositions of the present invention may optionally comprise a flavonoid compound. Flavonoids are broadly disclosed in U.S. Pat. Nos. 5,686,082 and 5,686,367, both of which are herein incorporated by reference.

The herein described flavonoid compounds are preferably present in the instant invention at concentrations of from about 0.01% to about 20%, more preferably from about 0.1% to about 10%, and most preferably from about 0.5% to about 5%.

(f) Anti-Inflammatory Agents

A safe and effective amount of an anti-inflammatory agent may be added to the compositions of the present invention, preferably from about 0.1% to about 10%, more preferably from about 0.5% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency. Anti-inflammatories can selected from several classes. One is comprised of steroidal anti-inflammatory agents, including but not limited to, corticosteroids. The preferred steroidal anti-inflammatory for use is hydrocortisone.

A second class of anti-inflammatory agents, which is useful in the compositions, includes the nonsteroidal anti-inflammatory agents. Such compounds are known in the art as non-steroidal anti-inflammatory agents ("NSAIDS") and are described in detail, along with methods for manufacture in the following U.S. Pat. Nos. 5,280,045; 4,708,966; 5,189,066; 5,510,361; 5,189,066; 5,476,876; and 5,684,204, all of which are incorporated herein by reference.

Mixtures of these non-steroidal anti-inflammatory agents may also be employed, as well as the dermatologically acceptable salts and esters of these agents.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms). For example, candelilla wax, alpha-bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Additional anti-inflammatory agents useful herein include allantoin and compounds of the Licorice (the plant genus/species *Glycyrrhiza glabra*) family, including glycyrrhetic acid, glycyrrhizic acid, and derivatives (e.g., salts and esters). Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

The active component of these anti-inflammatory agents (e.g., biabolol, glycyrrhetinate esters) may also be obtained via extraction from natural sources or prepared synthetically.

(g) Anti-Cellulite Agents

The compositions of the present invention may also comprise a safe and effective amount of an anti-cellulite agent. Suitable agents may include, but are not limited to, xanthine compounds (e.g., caffeine, theophylline, theobromine, and aminophylline).

(h) Topical Anesthetics

The compositions of the present invention may also comprise a safe and effective amount of a topical anesthetic. Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

(i) Tanning Actives

The compositions of the present invention may comprise a tanning active. When present, it is preferable that the compositions comprise from about 0.1% to about 20%, more preferably from about 2% to about 7%, and most preferably from about 3% to about 6%, by weight of the composition, of dihydroxyacetone as an artificial tanning active.

Dihydroxyacetone is also known to be more stable at acidic pH values. See *The Merck Index*, Tenth Edition, entry 3167, p. 463 (1983), and "Dihydroxyacetone for Cosmetics", E. Merck Technical Bulletin, 03-304 110, 319 897, 180 588.

(j) Skin Lightening Agents

The compositions of the present invention may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include those known in the art, including kojic acid, arbutin, tranexamic acid, ascorbic acid and derivatives, e.g., magnesium ascorbyl phosphate or sodium ascorbyl phosphate or other salts of ascorbyl phosphate. Skin lightening agents suitable for use herein also include those described in copending patent application Ser. No. 08/479,935, filed on Jun. 7, 1995 in the name of Hillebrand, corresponding to PCT Application No. U.S. 95/07432, filed Jun. 12, 1995; and copending patent application Ser. No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. 95/02809, filed Mar. 1, 1995, published Sep. 8, 1995.

(k) Antimicrobial and Antifungal Actives

The compositions of the present invention may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and most preferably from about 0.05% to about 2%.

(l) Sunscreen Actives

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206-38269, Aug. 25, 1978.

Also particularly useful in the compositions are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreening agents disclosed therein have, in a single molecule, two distinct chromophore moieties, which exhibit different ultra-violet radiation absorption spectra. One of the chromophore moieties absorbs predominantly in the UVB radiation range and the other absorbs strongly in the UVA radiation range.

(m) Conditioning Agents

The compositions of the present invention may comprise a conditioning agent selected from the group consisting of humectants, moisturizers, or skin conditioners. A variety of these materials can be employed and each can be present at a level of from about 0.01% to about 20%, more preferably from about 0.1% to about 10%, and most preferably from about 0.5% to about 7% by weight of the composition. These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fructose, sucrose, etc.); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990.

Also useful are various $C_1$-$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al., issued Jun. 15, 1976; U.S. Pat. No. 4,518,772, to Volpenhein, issued May 21, 1985; and U.S. Pat. No. 4,517,360, to Volpenhein, issued May 21, 1985.

Preferably, the conditioning agent is selected from the group consisting of glycerol, urea, guanidine, sucrose polyester, and combinations thereof.

(n) Thickening Agent (Including Thickeners and Gelling Agents)

The compositions of the present invention can comprise one or more thickening agents, preferably from about 0.1% to about 5%, more preferably from about 0.1% to about 3%, and most preferably from about 0.25% to about 2%, by weight of the composition.

Nonlimiting classes of thickening agents include those selected from the group consisting of:

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; and in *CTFA International Cosmetic Ingredient Dictionary*, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from the group consisting of carbomers, acrylates/$C_{10}$-$C_{30}$ alkyl acrylate crosspolymers, and mixtures thereof.

(ii) Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987.

(iii) Polyacrylamide Polymers

The compositions of the present invention can optionally comprise polyacrylamide polymers, especially nonionic polyacrylamide polymers including substituted branched or unbranched polymers. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR$_{150}$H, SS500V, SS500W, SSSA100H, from Lipo Chemicals, Inc., (Patterson, N.J.).

(iv) Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses.

Other useful polysaccharides include scleroglucans comprising a linear chain of (1-3) linked glucose units with a (1-6) linked glucose every three units, a commercially available example of which is Clearogel™ CS11 from Michel Mercier Products Inc. (Mountainside, N.J.).

(v) Gums

Other thickening and gelling agents useful herein include materials that are primarily derived from natural sources. Nonlimiting examples of these gelling agent gums include materials selected from the group consisting of acacia, agar, algin, alginic acid, ammonium alginate, amylopectin, calcium alginate, calcium carrageenan, camitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Preferred compositions of the present invention include a thickening agent selected from the group consisting of carboxylic acid polymers, crosslinked polyacrylate polymers, polyacrylamide polymers, and mixtures thereof, more preferably selected from the group consisting of carboxylic acid polymers, polyacrylamide polymers, and mixtures thereof.

It is preferred that the composition of the present invention comprise an additional skin care active that is present in an amount of from about 0.001% to about 10%, by weight of the composition, preferably from about 0.01% to about 7%, and most preferably from about 0.025% to about 5%.

Composition Preparation

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. The compositions are preferably prepared such as to optimize stability (physical stability, chemical stability, photostability) and/or delivery of the active materials (e.g., agmatine, BHT or BHA, and an additional skin care active selected from the group consisting of hexamidines, cetyl pyridinium chlorides, phytosterols, ursolic acids, and green tea catechins,). This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic applications continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions, which are typically applied per application, are, in mg composition/cm$^2$ skin, from about 0.1 mg/cm$^2$ to about 20 mg/cm$^2$. A particularly useful application amount is about 0.5 mg/cm$^2$ to about 10 mg/cm$^2$.

Methods for Regulating Skin Condition

The compositions of the present invention are useful for regulating keratinous tissue, particularly hair growth and mammalian skin condition. Such regulation of keratinous tissue conditions can include prophylactic and therapeutic regulation. It may also include providing a more noticeable improvement, both tactile and visual, in the appearance and feel of the hair on the kin of a mammal. For example, such regulating methods are directed to making the hair appear softer, finer, and/or less noticeable. Also, such methods provide ease, frequency, and effectiveness of shaving on a mammal. Examples of regulating skin conditions include, but are not limited to thickening keratinous tissue (i.e., building the epidermis and/or dermis layers of the skin and where applicable the keratinous layers of the nail and hair shaft) and preventing and/or retarding atrophy of mammalian skin, preventing and/or retarding the appearance of spider vessels and/or red blotchiness on mammalian skin, treating (i.e. preventing and/or retarding the appearance of) dark circles under the eye of a mammal, preventing and/or retarding sallowness of mammalian skin, regulating (i.e. preventing and/or retarding) sagging of mammalian skin, softening and/or smoothing lips, hair and nails of a mammal, preventing and/or relieving itch of mammalian skin, regulating skin texture (e.g. wrinkles and fine lines), regulating the appearance of shiny skin, treating (i.e. preventing and/or retarding the appearance of) cellulite, increasing the rate of skin turnover, and improving skin color (e.g. redness, freckles).

Regulating keratinous tissue condition involves topically applying to the keratinous tissue a safe and effective amount of a composition of the present invention. The amount of the composition which is applied, the frequency of application and the period of use will vary widely depending upon the level of skin care actives and/or other components of a given composition and the level of regulation desired, e.g., in light of the level of keratinous tissue damage present or expected to occur.

In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions which are typically applied per application are, in mg composition/cm$^2$ skin, from about 0.1 mg/cm$^2$ to about 10 mg/cm$^2$. A particularly useful application amount is about 1 mg/cm$^2$ to about 2 mg/cm$^2$.

Regulating keratinous tissue condition is preferably practiced by applying a composition in the form of a skin lotion, cream, gel, foam, ointment, paste, serum, stick, emulsion, spray, conditioner, tonic, cosmetic, lipstick, foundation, nail polish, after-shave, or the like which is preferably intended to be left on the keratin structure for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, still more preferably for at least several hours, e.g., up to about 12 hours. Any part of the external portion of the face, hair, and/or nails can be treated, e.g., face, lips, under-eye area, upper lip, eyelids, scalp, neck, torso, arms, underarms, hands, legs, feet, fingernails, toenails, scalp hair, eyelashes, eyebrows, etc. The composition can be applied with the fingers or with an implement or device (e.g., pad, cotton ball, applicator pen, spray applicator, and the like).

Another approach to ensure a continuous exposure of the skin to at least a minimum level of the skin care active is to apply the compound by use of a patch applied, e.g., to the face. Such an approach is particularly useful for problem skin areas needing more intensive treatment (e.g., facial crows feet area, frown lines, under eye area, upper lip and the like). The patch can be occlusive, semi-occlusive or non-occlusive and can be adhesive or non-adhesive. The composition can be contained within the patch or be applied to the skin prior to application of the patch. The patch can also include additional actives such as chemical initiators for exothermic reactions such as those described in U.S. Pat. Nos. 5,821,250, 5,981, 547, and 5,972,957 to Wu, et al. The patch is preferably left on the skin for a period of at least about 5 minutes, more preferably at least about 15 minutes, more preferably still at least about 30 minutes, even more preferably at least about 1 hour, still more preferably at night as a form of night therapy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Skin Cream

Examples 1-5

A moisturizing skin cream/lotion is prepared by conventional methods from the following components.

|  | Example | | | | |
|---|---|---|---|---|---|
| Component | 1 | 2 | 3 | 4 | 5 |
| Phase A | | | | | |
| Water | qs | Qs | qs | qs | qs |
| Glycerol | 5.0000 | 7.0000 | 7.0000 | 10.0000 | 5.0000 |

-continued

| Component | Example 1 | 2 | 3 | 4 | 5 |
|---|---|---|---|---|---|
| phenylbenzimidazole sulfonic acid | 0 | 0 | 0 | 0 | 1.2500 |
| disodium EDTA | 0.1000 | 0.1000 | 0.1000 | 0.1000 | 0.1000 |
| Allantoin | 0.2000 | 0.2000 | 0.2000 | 0.2000 | 0.2000 |
| Triethanolamine | 0 | 0 | 0 | 0 | 0.7500 |
| sodium metabisulfite | 0.1000 | 0.2000 | 0.1000 | 0.1000 | 0.1000 |
| BHT | 0.50 | 0.50 | 0.50 | 0.50 | 0.50 |
| titanium dioxide | 0.2500 | 0.4500 | 0.4500 | 0.7500 | 0.5500 |
| Niacinamide | 0 | 0 | 2.0000 | 3.5000 | 2.0000 |
| Dexpanthenol | 0.25 | 0.5000 | 1.0000 | 2.0000 | 1.0000 |
| palmitoyl-pentapeptide[1] | 0 | 0 | 0.0004 | 0 | 0.0003 |
| C12-C15 alkyl benzoate | 5.00 | 2.5000 | 1.5000 | 2.5000 | 0 |
| caprylic/capric triglyceride | 1.0 | 1.5000 | 1.5000 | 1.5000 | 1.5000 |
| Farnesol | 0 | 0.5000 | 5.0000 | 3.0000 | 3.0000 |
| octyl salicylate | 0 | 0 | 0 | 0 | 5.0000 |
| Octocrylene | 0 | 0 | 0 | 0 | 1.0000 |
| butyl methoxy-dibenzoylmethane | 0 | 0 | 0 | 0 | 2.0000 |
| cetyl alcohol | 0.5000 | 0.5000 | 0.5000 | 0.5000 | 0.5000 |
| tocopherol acetate | 0 | 0.5000 | 0.5000 | 0.5000 | 0.5000 |
| tocopherol sorbate | 0.5000 | 0 | 0 | 0.5000 | 0.2000 |
| sorbitan stearate/sucrose cocoate | 1.0000 | 1.0000 | 1.0000 | 1.0000 | 1.0000 |
| cetearyl glucoside | 0.5000 | 0.5000 | 0.5000 | 0.5000 | 0.5000 |
| stearyl alcohol | 0.7000 | 0.7000 | 0.7000 | 0.7000 | 0.7000 |
| behenyl alcohol | 0.6000 | 0.6000 | 0.6000 | 0.6000 | 0.6000 |
| ethyl paraben | 0.2000 | 0.2000 | 0.2000 | 0.2000 | 0.2000 |
| propyl paraben | 0.1000 | 0.1000 | 0.1000 | 0.1000 | 0.1000 |
| PEG-100 stearate | 0.1000 | 0.1000 | 0.1000 | 0.1000 | 0.1000 |
| Polymethyl-silsesquioxane | 0.2500 | 0.5000 | 1.5000 | 0.5000 | 0.2500 |
| Phase C | | | | | |
| polyacrylamide/C13-14 isoparaffin/laureth-7 | 2.000 | 2.2500 | 2.5000 | 2.5000 | 3.0000 |
| Phase D | | | | | |
| agmatine | 2.5000 | 2.5000 | 2.5000 | 2.5000 | 2.5000 |
| green tea extract | 1.0000 | 1.0000 | 1.0000 | 1.0000 | 0 |
| BHT | 0.50 | 0.50 | 0.50 | 0.50 | 0.50 |
| benzyl alcohol | 0.2500 | 0.2500 | 0.2500 | 0.2500 | 0.2500 |
| dimethicone/dimethiconol | 0.5 | 1.0000 | 2.5000 | 0.2500 | 2.0000 |
| Perfume | 0.2000 | 0.2000 | 0.2000 | 0.2000 | 0.2000 |

[1]palmitoyl-pentapeptide = palmitoyl-lysine-threonine-threonine-lysine-serine available from Sederma.

In a suitable vessel, the Phase A components are combined and mixed with a suitable mixer (e.g., Tekmar RW20DZM) and heated with stirring to a temperature of about 70-80° C. and this temperature is maintained. In a separate suitable vessel, the Phase B components are combined and mixed with a suitable mixer and are heated with stirring to about 70-75° C. and this temperature is maintained. The Phase B mixture is then added to the Phase A mixture and mixed well so as to emulsify the combination. The emulsion of Phase A and B components is then allowed to cool to about 60° C. and then the Phase C components are to the emulsion with continuous mixing. The emulsion of Phase A, B and C components is then allowed to further cool to about 40° C., and then the Phase D components are added with mixing to the emulsion. The resulting emulsion is then milled using a suitable mill (Tekmar T-25) for about 5 minutes or until the product is uniform.

Examples 6-8

A moisturizing skin cream/lotion for hand and body skin care is prepared by conventional methods from the following components.

The following examples further describe and demonstrate embodiments within the scope of the present invention. They are given for the purpose of illustration and are not to be construed as limitations of the present invention. Where applicable, ingredients are given in CTFA name. All of the examples are oil-in-water emulsions prepared using conventional formulating techniques. The coated titanium dioxide is incorporated via the oil phase ingredients whereas the nylon particles and interference pigment are added via the aqueous phase.

| Component | Example 6 % w/w | 7 % w/w | 8 % w/w |
|---|---|---|---|
| Niacinamide | 2.0 | 4.0 | 6.0 |
| Retinyl Propionate | | 0.2 | |
| Panthenol | 1.0 | 2.0 | 0.5 |
| Polyacrylamide & isoparaffin & laureth-7 | 2.0 | 2.25 | 2.25 |
| Glycerine | 5.0 | 3.0 | 7.0 |
| Allantoin | 0.2 | 0.05 | 0.1 |
| Aloe vera gel | 0.05 | 0.075 | 0.05 |
| Tocopheryl acetate | 0.75 | 0.5 | 0.5 |
| Cetyl alcohol | 2.0 | 1.0 | 1.25 |
| Stearyl alcohol | 2.0 | 1.0 | 1.25 |
| Behenyl alcohol | 1.0 | 1.0 | 1.25 |
| Dimethicone & dimethiconol | 0.75 | 0.5 | 0.50 |
| Steareth-21 | 0.6 | 0.4 | 0.5 |
| Steareth-2 | 0.1 | 0.08 | 0.03 |
| PPG-15 stearyl ether | 3.0 | 2.0 | 1.00 |
| Isohexadecane | 0 | 7.0 | 5.0 |
| agmatine | 2.50 | 2.50 | 2.50 |
| Isononyl isononanoate | 5.0 | 0 | 0 |
| Dimethicone (350 mm$^2$s$^{-1}$) | 0.5 | 0.0 | 0.60 |
| Disodium EDTA | 0.10 | 0.10 | 0.10 |
| Nylon 12[1] | 1.5 | 1.0 | 1.1 |
| Titanium Dioxide (and) Mica[2] | 0.75 | 1.5 | 1.25 |
| BHT | 0.50 | 0.50 | 0.50 |
| Petrolatum | 1.00 | 4.00 | 2.00 |
| Deionised water, fragrance, presevatives | to 100% | to 100% | to 100% |

[1]Orgasol ® 2002 D NAT COS.
[2]A green interference pigment

Antiperspirant/Deodorants

Examples 9-12

An antiperspirant soft solid/cream is prepared by conventional methods from the following components.

| Component | Example 9 | 10 | 11 | 12 |
|---|---|---|---|---|
| Al Zr Trichlorohydrex Glycinate (solid) | 25.25 | 25.25 | 25.25 | 25.25 |
| Dimethicone (10 cs) | 5.00 | 5.00 | 5.00 | 5.00 |
| Fully Hydrogenated High Erucic Acid Rapeseed oil (HEAR oil) | 5.00 | 5.00 | 5.00 | 5.00 |
| agmatine | 2.50 | 2.50 | 2.50 | 2.50 |
| C-18-36 Acid Triglyceride Syncrowax HGLC | 1.25 | 1.25 | 1.25 | 1.25 |
| Perfume | 0.75 | 0.75 | 0.75 | 0.75 |
| Calcium Pantothenate (solid) | 0.50 | 0 | 3.50 | 0 |

-continued

| Component | Example | | | |
|---|---|---|---|---|
| | 9 | 10 | 11 | 12 |
| BHT | 0.50 | 0.50 | 0.50 | 0.50 |
| Tocopherol Acetate | 0.50 | 0 | 0.50 | 0 |
| Cyclopentasiloxane | QS | QS | QS | QS |
| Total | 100.00 | 100.00 | 100.00 | 100.00 |

Example 13

A foundation compact of the present invention comprising cross-linked siloxane elastomer is prepared as follows:

| Ingredient | wt. % |
|---|---|
| TiO2 silicone treated (SAT treated Tronox CR 837 supplied US Cosmetics) | 5.25 |
| Pigment | 1.23 |
| Talc (silicone treated) (Hydrophobic Talc 9742 supplied by Warner Jenkinson) | 2.36 |
| Agmatine | 2.50 |
| TiO2-MT100T (micronized TiO2 supplied by Tri-K) | 0.16 |
| DC245 (cyclomethicone) | 29.26 |
| DC5225C (dimethicone copolyol - 10% active in cyclomethicone) | 0.31 |
| GE SFE 839 Cross-linked Siloxane Elastomer Gel[1] | 48 |
| propylparaben (preservative) | 0.10 |
| BHT | 0.50 |
| Glycerine | 7.08 |
| Ozokerite Wax | 3.25 |
| Total: | 100.00 |

[1] 5% Dimethicone/vinyl dimethicone cross-polymer in cyclomethicone

In a suitable vessel equipped with a heating source, the pigments, $TiO_2$ (micronized and silicone treated), hydrophobic talc, GE SFE 839, cyclomethicone (DC245) and dimethicone copolyol (DC5225C) are mixed until homogeneous and then milled using a Silverson L4RT mixer at 9000 rpms to the desired particle size. Next, the propylparaben and glycerine are added to the above mixture and mixed until homogenous. The mixture is then heated to a temperature of between 85-90° C., at which time the ozokerite wax is added (melted into the mixture) with mixing until the mixture homogenous. The mixture is then poured into a mold and allowed to cool at room temperature. Once cooled, the mixture incorporated into the appropriate package.

The foundation compact is applied to the face to provide color, moisturization and improved feel.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inhibiting mammalian hair growth, said method comprising the step of:
   chronically applying a safe and effective amount of a personal care composition to an area of keratinous tissue wherein inhibition of hair growth is desired, the personal care composition comprising a safe and effective amount of butylated hydroxytoluene, and a safe and effective amount of agmatine,
   wherein the step of chronically applying the personal care composition is performed for a time period of at least one complete hair growth cycle, so that hair follicles at different growth stages within the area of keratinous tissue wherein inhibition of hair growth is desired are exposed to the composition prior to or during the anagen stage of the hair growth cycle.

2. The method of claim 1, wherein the composition further comprises niacinamide.

3. The method of claim 1, wherein the composition further comprises panthenol.

4. The method of claim 1, wherein the composition further comprises tocopheryl acetate.

5. The method of claim 1, wherein the composition comprises about 0.5 weight percent of the butylated hydroxytoluene.

* * * * *